(12) United States Patent
Liu

(10) Patent No.: US 10,775,646 B2
(45) Date of Patent: Sep. 15, 2020

(54) INTELLIGENT TEMPERATURE- AND HUMIDITY-CONTROL VISIBLE MULTI-FUNCTION EYE-CARE MASSAGE GLASSES

(71) Applicant: Dongguang Liu, Guangdong (CN)

(72) Inventor: Dongguang Liu, Guangdong (CN)

( * ) Notice: Subject to any disclaimer, the term of this patent is extended or adjusted under 35 U.S.C. 154(b) by 974 days.

(21) Appl. No.: 15/352,603

(22) Filed: Nov. 16, 2016

(65) Prior Publication Data

US 2017/0139235 A1 May 18, 2017

Related U.S. Application Data

(63) Continuation-in-part of application No. PCT/JP2015/083390, filed on Jul. 6, 2015.

(30) Foreign Application Priority Data

May 21, 2015 (CN) ..................... 2015 2 0332895 U

(51) Int. Cl.
*G02C 11/00* (2006.01)
*A61F 9/02* (2006.01)
(Continued)

(52) U.S. Cl.
CPC .............. *G02C 11/00* (2013.01); *A61F 7/007* (2013.01); *A61F 7/0085* (2013.01); *A61F 9/00* (2013.01); *A61F 9/02* (2013.01); *A61H 9/0078* (2013.01); *G02C 7/16* (2013.01); *G02C 11/08* (2013.01); *A61F 2007/0004* (2013.01); *A61F 2007/0071* (2013.01); *A61F 2007/0086* (2013.01); *A61F 2007/0091* (2013.01);
(Continued)

(58) Field of Classification Search
CPC .. A61F 9/02; A61F 9/026; A61F 9/029; A61F 9/04; A61F 2007/0004; G02C 11/00; G02C 11/08; A61H 9/0078; A61H 9/0092; A61H 23/002–2023; A61H 2205/022; A61H 2205/025; A61H 5/00
See application file for complete search history.

(56) References Cited

U.S. PATENT DOCUMENTS

| 6,155,995 | A | * | 12/2000 | Lin | ........................... A61F 7/02 601/148 |
| 2005/0022823 | A1 | * | 2/2005 | Davison | ................. A61F 9/029 128/858 |

(Continued)

*Primary Examiner* — Valerie L Woodward

(57) ABSTRACT

A pair of intelligent temperature- and humidity-control visible multi-function eye-care massage glasses, having blinders in which they are equipped with windows and control circuits, and also having heating devices and humidity-control devices equipped at the peripheries of the windows, wherein the control circuits are electrically connected to the heating devices and the humidity-control devices respectively. The beneficial effects of the present invention: it does not press on the eyeballs, so as to avoid causing or aggravating eye diseases; it provides intelligent temperature- and humidity-control devices, which can effectively ameliorate eye discomfort; people can work or recreate as usual when wearing it, which is good for long-term wear so as to achieve a good long-term effect. It also has balloon-like airbags, which can more effectively stimulate the meridian points of the eyes so as to enhance the massage effect.

11 Claims, 5 Drawing Sheets

(51) Int. Cl.
*A61F 7/00* (2006.01)
*A61F 9/00* (2006.01)
*A61H 9/00* (2006.01)
*G02C 7/16* (2006.01)
*G02C 11/08* (2006.01)
*A61H 23/02* (2006.01)
*A61F 7/02* (2006.01)

(52) U.S. Cl.
CPC ...... *A61F 2007/0228* (2013.01); *A61H 23/02* (2013.01); *A61H 2201/0192* (2013.01); *A61H 2201/0207* (2013.01); *A61H 2201/0214* (2013.01); *A61H 2201/0228* (2013.01); *A61H 2201/0242* (2013.01); *A61H 2201/105* (2013.01); *A61H 2201/12* (2013.01); *A61H 2201/1604* (2013.01); *A61H 2201/165* (2013.01); *A61H 2201/169* (2013.01); *A61H 2201/50* (2013.01); *A61H 2201/5046* (2013.01); *A61H 2201/5048* (2013.01); *A61H 2201/5082* (2013.01); *A61H 2205/024* (2013.01)

(56) References Cited

U.S. PATENT DOCUMENTS

| | | | | |
|---|---|---|---|---|
| 2014/0251342 | A1* | 9/2014 | O'Brien | A61F 9/068 128/847 |
| 2014/0336565 | A1* | 11/2014 | Nichols | A61M 11/005 604/24 |
| 2015/0121610 | A1* | 5/2015 | Cornelius | A61F 9/04 2/435 |
| 2016/0044747 | A1* | 2/2016 | Prins | H05B 3/86 219/211 |
| 2016/0051439 | A1* | 2/2016 | Brown | A61H 21/00 601/46 |
| 2016/0262936 | A1* | 9/2016 | Belliappa | A61F 9/04 |
| 2017/0266035 | A1* | 9/2017 | Kuo | A61F 7/007 |
| 2018/0280190 | A1* | 10/2018 | Betkowski | A41D 13/0051 |

* cited by examiner

INTELLIGENT TEMPERATURE- AND HUMIDITY-CONTROL VISIBLE MULTI-FUNCTION EYE-CARE MASSAGE GLASSES

BACKGROUND OF THE INVENTION

The present invention relates generally to health care devices, and more particularly, to a pair of temperature- and humidity-control visible multi-function eye-care massage glasses.

With the popularity of computers and mobile electronic devices, people are in contact with electronic screens almost every day. After prolonged use of these devices, it will cause harmful impact on the human eyes; therefore, a variety of eye massage devices have been launched into the current market for consumers to alleviate or ameliorate symptoms arising from the excessive use of their eyes. However, it needs to be noted that the currently available eye heating and pressure massage devices, etc., mainly have the following shortcomings or limitations:

1. The Massage Devices' Directly Pressing Against the Eyeballs is Likely to Aggravate Some Serious Eye Diseases (1) Dry eye syndrome is a common eye disease. It mainly is shown as eye fatigue, eye dryness, foreign body sensation, eye irritation, photophobia, tearing and other symptoms. If these devices directly press the eyes of such patients for massage, it can bruise the corneal epithelium and aggravate the diseases. Dry eye syndrome commonly causes dotted or flaked deletion or erosion of corneal epithelial cells, so squeezing of the cornea should be prevented.

(2) For patients suffering from dry eye syndrome associated with ocular hypertension, retinal ischemia, or hemorrhagic lesions, such as glaucoma, hypertension, or diabetic retinopathy, the direct press and massage on their eyeballs may aggravate the retinal ischemia or bleeding. That will cause serious consequences.

2. Temperature Effect on the Eyes is not Constant

Most human eyes can tolerate thermotherapy with temperatures ranging from 38 to 45 degrees centigrade. According to some studies in the field of ophthalmology, the temperature of 42 degrees centigrade generates a relatively good effect of thermotherapy on human eyes. It helps the heat penetrate deep into the eyeballs, thus promoting blood circulation and tissue metabolism. It also helps liquefy the meibomian gland lipid so as to provide an anti-dry protective layer of lipid for the cornea. However, the currently available eye heating massage devices all have no thermostats for the eyeballs. The temperatures vary, and are not constant.

3. They Lack Eyeball Humidifying and Moisturizing Devices

As everyone knows, the main role of an eye massage device is to prevent eye fatigue. However, in the field of ophthalmology, most eye fatigues are attributed to dry eye syndrome caused by factors such as watching TV and computers, overusing eyes, failing to rest the eyes well, and suffering from endocrine disorders or senile degeneration. Therefore, humidifying or moisturizing eyeballs can quickly alleviate the symptoms. However, the hot-pack eye massage devices currently available on the market are almost all in short of that function.

4. They Lack Visibility

Nearly all currently available hot pack and massage devices for the eyes on the market have no visual windows, and they all work on the eyes when the eyes are closed. As mentioned above, they will aggravate the eye diseases. Besides, the long-term massage on closed eyes is likely to cause a sense of fear and discomfort after the massage is completed.

5. They are Inconvenient to Carry with

The currently available massage glasses generally have an integrated design. Meanwhile, they need multiple additional modules for integration, thus making the structures relatively large, which is inconvenient for users to carry with in daily life.

Therefore, it is necessary to improve the eye massage devices, which are based on currently available technologies, so as to create eye-care glasses which can not only treat eye diseases but also overcome the current limitations.

BRIEF SUMMARY OF THE INVENTION

In view of the limitations of the currently available technologies, the present invention is intended to provide intelligent temperature- and humidity-control visible multi-function eye-care massage glasses, which can realize the temperature- and humidity-control at the peripheries of the eyes through the equipped heating devices and humidity-control devices; which allow users to work as usual while wearing it over their eyes during the health care process through the equipped visual windows; which can further massage eyes through the equipped airbags and vibrating motors targeting the meridian points at the peripheries of the eyes; in addition, the present invention also provides a design with separated left and right blinders, and makes the left and right blinders rotate relatively through bolt positioning to realize foldability.

To achieve the purposes above, the present invention adopts the following technical solutions:

The present invention discloses intelligent temperature- and humidity-control visible multi-function eye-care massage glasses, comprising blinders in which they are equipped with windows and control circuits corresponding to eye positions, and also comprising heating devices and humidity-control devices equipped at the peripheries of the windows, wherein the control circuits are electrically connected to the heating devices and the humidity-control devices respectively.

It needs to be noted that the heating devices comprise carbon fiber heating filaments and temperature sensors, the peripheries of the windows are provided with grooves used to install the carbon fiber heating filaments, and the carbon fiber heating filaments and the temperature sensors are electrically connected to the control circuits respectively.

It needs to be further noted that the humidity-control device comprises an adjusting chamber, a humidity-control upper leaf, a humidity-control lower leaf, a water storage sponge and humidity sensors, wherein the humidity-control upper leaf and the humidity-control lower leaf are flexibly connected to the top and bottom of the adjusting chamber respectively, the water storage sponge is distributed on side walls inside the adjusting chamber, and the humidity sensors and the control circuits are electrically connected.

It needs to be further noted that the top and bottom of the adjusting chamber are respectively equipped with a humidity-control groove used to expel the humidity in the adjusting chamber.

As a preferable technical solution, the top and bottom of the adjusting chamber are respectively equipped with an upper guide groove and a lower guide groove, and the humidity-control upper leaf and the humidity-control lower leaf are flexibly connected into the upper guide groove and the lower guide groove respectively; the water storage sponge can be equipped in a semi-closed space formed by the upper guide groove and the lower guide groove.

It needs to be further noted that the upper guide groove and the lower guide groove are equipped with a positioning bar respectively, and the humidity-control upper leaf or the humidity-control lower leaf is equipped with positioning grooves matched with the positioning bars.

As a preferable technical solution, the blinders are also equipped with a massage airbag device inside, and the massage airbag device comprises airbags, an air pump and a solenoid valve, wherein the airbags are connected to one end of the solenoid valve, one end of the air pump is connected to anther end of the solenoid valve, and the control circuits are electrically connected to the air pump and the solenoid valve respectively.

As a preferable technical solution, the blinders are also equipped with a vibrating motor inside which is electrically connected to the control circuits.

It needs to be noted that one side of the adjusting chamber is equipped with three-way pipes which are connected to the water storage sponge.

As a preferable technical solution, the blinders comprise a left blinder, a right blinder and a rotating device, wherein the left blinder and the right blinder are equipped with bolt holes at the opposite sides; the rotating device consists of a bolt and a rotating cap, and the bolt is connected into the bolt holes, to make the left blinder and the right blinder rotate along the bolt.

As an alternative structure, the humidity-control devices comprise fixing holes equipped on two sides of the glasses, lugs equipped on the two sides of the eye cups respectively and corresponding to the fixing holes, knob screws and springs. The springs are disposed between the fixing holes and the lugs, the lugs also have mounting holes, and the knob screws pass through the fixing holes and the springs so as to be screwed with the mounting holes.

It needs to be further noted that the nuts of the knob screws feature a regular polygon structure.

Another variation based on the present invention is visible heating integrated health care glasses, comprising shells, control boxes and head fixing parts. The shells and the head fixing parts are connected. The shells are provided with lens holes in which eye cups are equipped. The eye cups are provided with a lens in the front, and heating blinders at the back, while the shells are equipped with vibrating motors inside, and the heating blinders and the vibrating motors are connected with the control boxes through cables; between the blinders and eye cups, it is also disposed with anti-fog channels and humidity-control devices.

Preferably, the control boxes and the head fixing parts are connected, with the shells and the control boxes equipped face to face.

Preferably, the anti-fog channel is a space 0.5-3 mm in width.

Preferably, the lens can be removably mounted in front of the eye cups.

Preferably, the heating blinders comprise tubular blinder bodies. The tubular blinder bodies comprise heating parts. The heating parts comprise ring grooves and heating rings equipped therein.

Preferably, the blinder bodies also comprise massage parts connected to the heating parts, and the massage parts comprise massage layers.

Preferably, the eye cups comprise tubular cup bodies which are hinged on the lens holes. The cup bodies are equipped with the lens in the front end, with its rear end snap-fitted with the heating blinders.

Preferably, the lens is a transparent lens, and the eye cups are transparent cups.

Preferably, the control box comprises a front cover and a back cover, between which it is provided with a control circuit board. The control circuit board is equipped with a switch button, an indicator light, a charging plug and lithium batteries. The control circuit board is connected via cables, vibrating motors and heating rings.

Preferably, the shell is divided into a front shell and a back shell, with the lens holes of the back shell hinged to the cup bodies; the head fixing parts are bandages which are divided into left bandages and right bandages. The front shell and the back cover of the control box are provided with bandage buckles on both the left and right sides, respectively. The front end of the left bandages and the front end of the right bandages are fixed on the bandage buckles equipped on both the left and right sides of the front shell. The rear end of the left bandages and the rear end of the right bandages are fixed on the bandage buckles equipped on both the left and right sides of the back cover of the control box.

The beneficial effects of the present invention:

1. It only presses the peripheries of the eyelids without pressing the eyeballs, so it can avoid causing and aggravating the common eye diseases mentioned above;

2. It provides intelligent eye cups which can keep the eyes at a constant temperature of about 42 degrees centigrade, and can adjust the moisture on the eyeballs according to the needs;

3. Users can watch computers and TV, and read or write with their eyes open when using it. It integrates the eye-care process into work and entertainment, which is good for long-term persistence so as to achieve a good long-term effect.

4. The airbags are disposed with dotted balloons corresponding to the meridian points at the peripheries of eyes, which can more effectively stimulate the meridian points of eyes so as to enhance the massage effect.

5. It is foldable, so it is convenient for users to carry with; meanwhile, it also saves the storage space.

Figure 1:
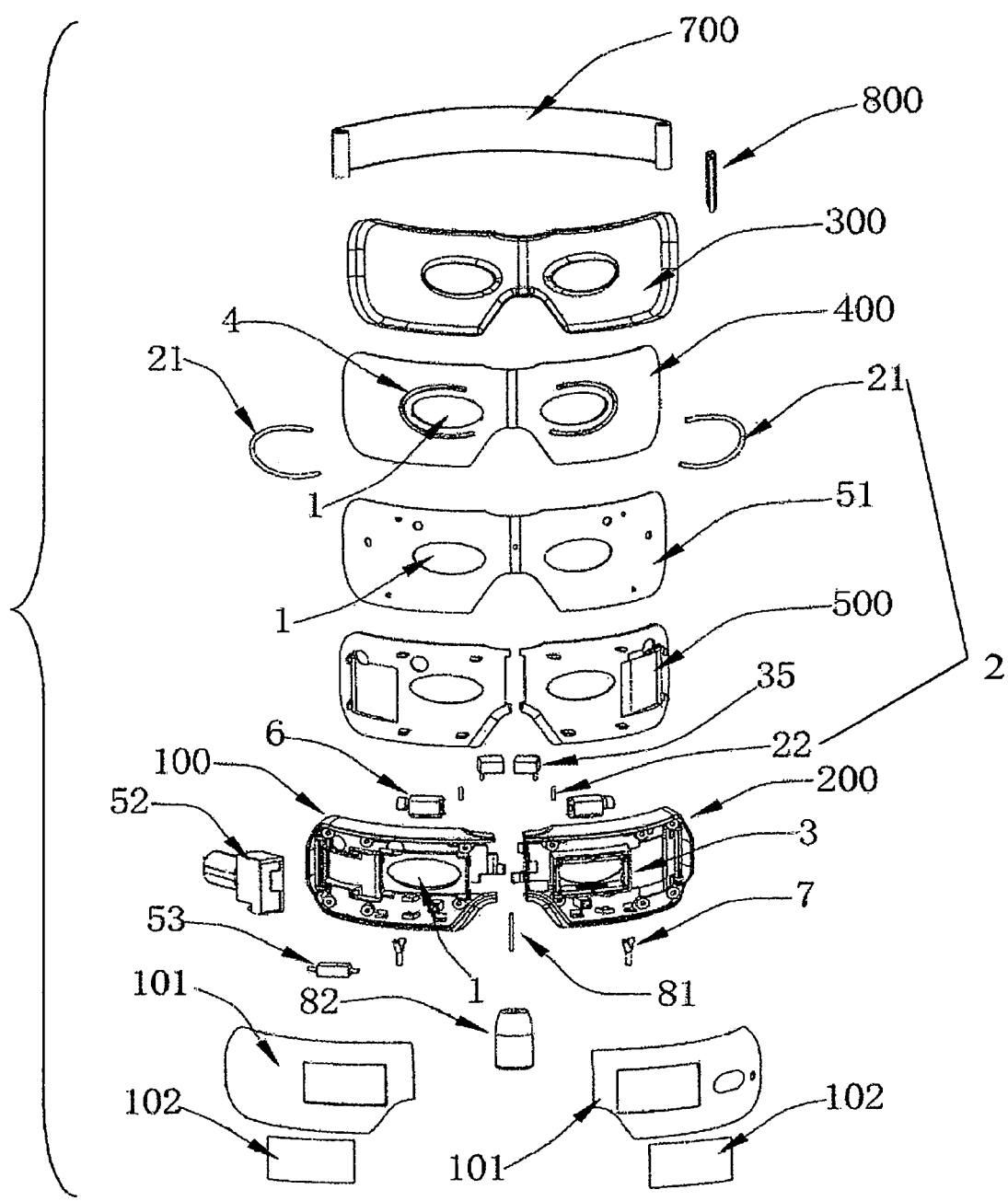
FIG. 1 is an exploded structural view of the utility model.

Marks in Figures: window 1; heating device 2; carbon fiber heating filament 21; temperature sensor 22; humidity-control device 3; adjusting chamber 31; humidity-control upper leaf 32; humidity-control lower leaf 33; water storage sponge 34; humidity sensors 35; positioning groove 36; anti-skid balloon 37; humidity-control groove 38; groove 4; massage airbag device 5; airbag 51; air pump 52; solenoid valve 53; vibrating motor 6; three-way pipe 7; rotating device 8; bolt 81; rotating cap 82; upper guide groove 311; lower guide groove 312; semi-closed space 313; positioning bar 314; left blinder 100; front cover 101; lens 102; right blinder 200; cloth 300; sponge pad 400; bag fixing plate 500; bolt hole 600; bandage 700; buckle 800; eye cup 501; lug 502; lens 601; fixing hole 602; knob screw 9; spring 91.

DETAILED DESCRIPTION OF THE INVENTION

Further descriptions of the present invention together with Figures are provided as follows. It needs to be noted that the embodiment gives detailed modes of execution and processes of operation on the premise of the technical solution, but the protective scope of the present invention is not limited to the embodiment.

As shown in FIG. 1, intelligent temperature- and humidity-control visible multi-function eye-care massage glasses, comprising blinders which comprise a left blinder 100 and a right blinder 200 in which they are equipped with windows 1 and control circuits corresponding to eye positions, and also comprising heating devices 2 (comprising carbon fiber heating filaments 21 and temperature sensors 22) and humidity-control devices 3 equipped at the peripheries of the windows 1, wherein the control circuits are electrically connected to the heating devices 2 and the humidity-control devices 3 respectively.

It needs to be noted that the eye-care glasses of the present invention can be provided with various pad layers, aiming to enhance the wearing comfort for users. As shown in FIG. 1, from the outer layer to the inner layer it is arranged with a cloth 300, sponge pad 400, and meanwhile, the airbags can be equipped on the surface of sponge pad 400, and fixed onto the left blinder 100 and right blinder 200 through the airbag fixing plate 500; in the meantime, the left blinder 100 and the right blinder 200 can be equipped with the front cover 101 on the surfaces, and the front cover 101 can be equipped with a window frame.

Furthermore, the window frame can be equipped with various lenses 102, which can enhance the health care effect in combination with other functions of the eye-care glasses.

As shown in FIG. 1, the heating devices 2 comprise carbon fiber heating filaments 21 and temperature sensors 22, the peripheries of the windows 1 are provided with grooves 4 which are used to install the carbon fiber heating filaments 21, and the carbon fiber heating filaments 21 and the temperature sensors 22 are electrically connected to the control circuits respectively.

Furthermore, as an example of the present invention shown in FIG. 1, the carbon fiber heating filaments 21 feature a semi-closed ring structure, which are mainly equipped at the peripheries of the eyes; however, as other modes of execution, the carbon fiber heating filaments also can be set as other shapes, with their position not limited to the peripheries of windows.

Figure 2:
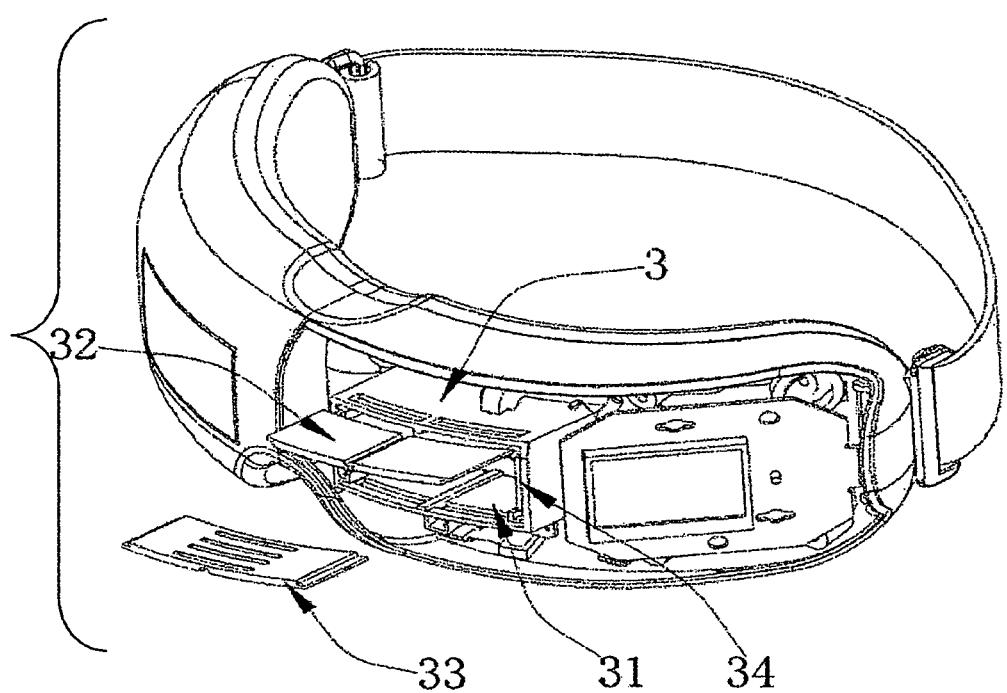
FIG. 2 is a structural view of the humidity-control device shown in FIG. 1.

As shown in FIG. 1 and FIG. 2, the humidity-control devices 3 comprise an adjusting chamber 31, a humidity-control upper leaf 32, a humidity-control lower leaf 33, a water storage sponge 34 and humidity sensors 35, wherein the humidity-control upper leaf 32 and the humidity-control lower leaf 33 are flexibly connected to the top and bottom of the adjusting chamber 31 respectively, the water storage sponge 34 is distributed on side walls inside the adjusting chamber 31, and the humidity sensors 35 and the control circuits are electrically connected.

Figure 3:
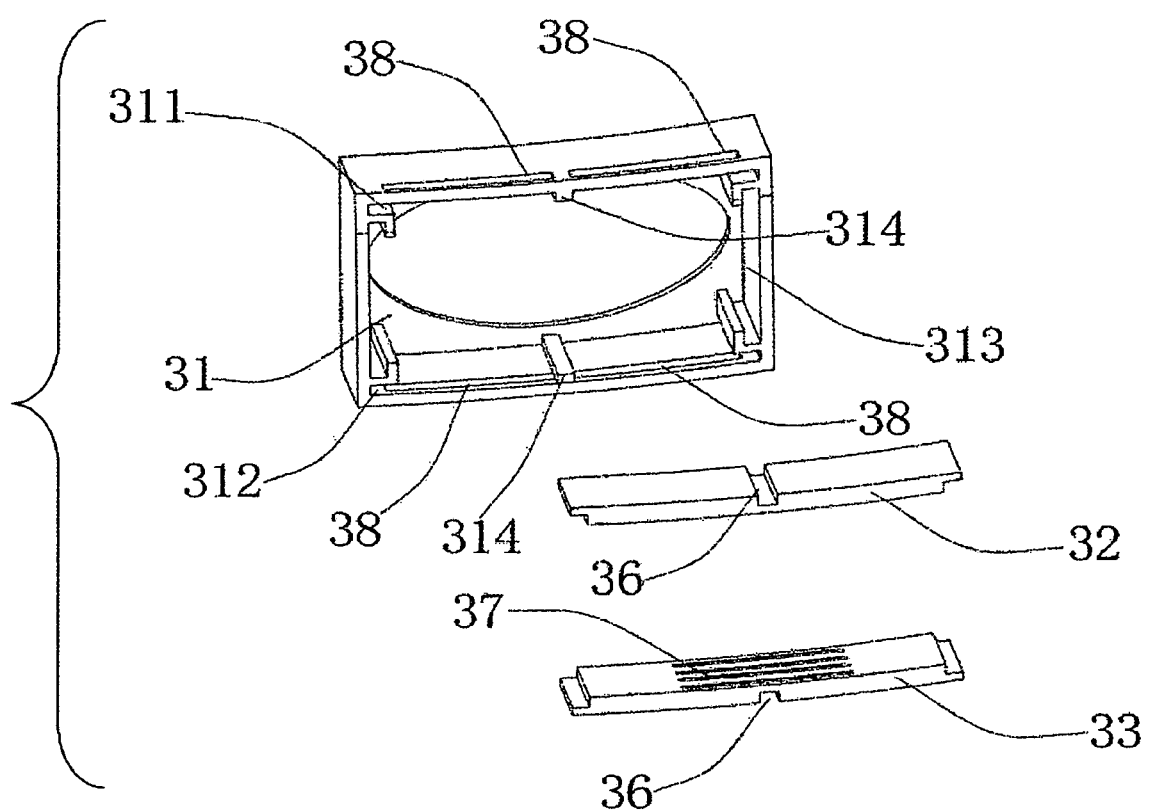
FIG. 3 is a structural view of the adjusting chamber shown in FIG. 2.

It needs to be further noted that, as shown in FIG. 3, the top and bottom of the adjusting chamber 31 are respectively equipped with the upper guide groove 311 and the lower guide groove 312, with the same structure but in opposite position, which are used to install the humidity-control upper leaf 21 or the humidity-control lower leaf 33, and the humidity-control upper leaf 32 or the humidity-control lower leaf 33 can slide forward and backward in the corresponding guide grooves; the water storage sponge can be equipped in a semi-closed space 313 formed by the upper guide groove and the lower guide groove.

It needs to be further noted that in order to prevent the possible dislocation of the humidity-control upper leaf 32 or the humidity-control lower leaf 33 when sliding in the corresponding grooves, positioning bars 314 may be provided in the upper guide groove 311 and the lower guide groove 312, and correspondingly, positioning grooves 36 matching with the positioning bars 314 may be provided in the humidity-control upper leaf 32 or the humidity-control lower leaf 33. In this way, it can prevent the dislocation during sliding.

As a preferable technical solution, as shown in FIG. 3, in order to help the users slide the humidity-control upper leaf 32 or the humidity-control lower leaf 33, anti-skid balloons 37 may be provided on the surfaces of both respectively.

It needs to be further noted that the top and bottom of the adjusting chamber 31 are respectively equipped with a humidity-control groove 38 used to discharge the humidity in the adjusting chamber 31; in a normal state, the humidity-control upper leaf or the humidity-control lower leaf are mismatched with the humidity-control groove so that the humidity in the adjusting chamber can be discharged through the humidity-control grooves; when sliding the corresponding humidity-control upper leaf or the humidity-control lower leaf, it can shield or partly shield the humidity-control grooves, so as to gather or slowly discharge the humidity out of the adjusting chamber.

It needs to be further noted that, as shown in FIG. 1, one side of the adjusting chamber is equipped with three-way pipes 7 connected to the sponge; furthermore, the left and right blinders are simultaneously equipped with through-holes connected to the three-way pipes, so as to add fluids that can form moisture.

As a preferable technical solution, as shown in FIG. 1, the blinders are also equipped with a massage airbag device 5 inside, and the massage airbag device 5 comprises airbags 51, an air pump 52 and a solenoid valve 53, wherein the airbags 51 are connected to one end of the solenoid valve 53, one end of the air pump 52 is connected to another end of the solenoid valve 53, and the control circuits are electrically connected to the air pump 52 and the solenoid valve 53 respectively.

As a preferable technical solution, as shown in FIG. 1, the blinders are also equipped with vibrating motors 6 inside which are electrically connected to the control circuits.

It needs to be further noted that the airbags are distributed according to the meridian points of human eyes, and preferably, the size of the airbags should be matched with the size of the meridian points mentioned above, so as to realize accurate massages on meridian points; of course, the airbags also can be formed in other shapes, such as a cube.

Figure 4:
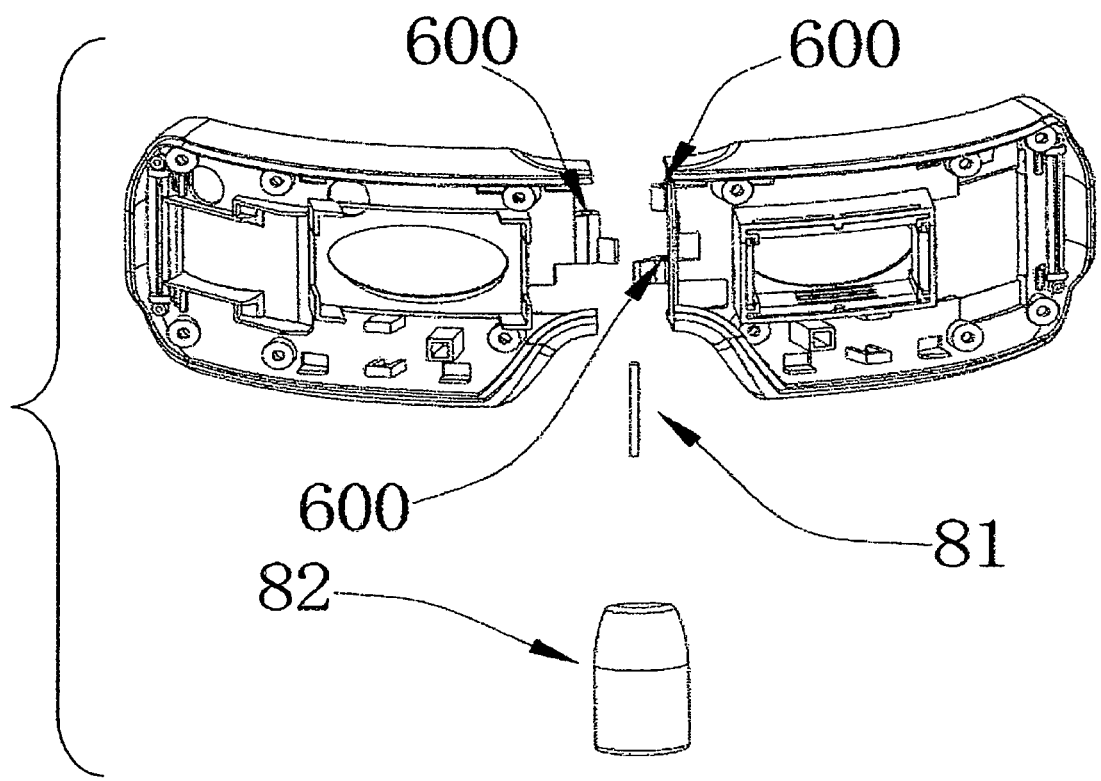
FIG. 4 is a structural view of the left and right blinders and the rotating device shown in FIG. 1.

As a preferable technical solution, as shown in FIG. 1 and FIG. 4, between the left blinder 100 and the right blinder 200 is a rotating device 8, wherein the left blinder 100 and the right blinder 200 are equipped with bolt holes 600 at the opposite sides; the rotating device 8 consists of a bolt 81 and a rotating cap 82, and the bolt 81 is connected into the bolt holes 600, to make the left blinder 100 and the right blinder 200 rotate along the bolt 81.

It needs to be noted that the connected structure formed by the way that the bolt passes through the bolt holes to flexibly connect the left blinder and the right blinder can be shielded by the rotating cap.

It needs to be further noted that for the convenience of wearing, the present invention is also provided with bandages 700 and buckles 800 used to adjust the length of the bandages.

It needs to be further noted that the control circuits comprise a microprocessor, and an LCD display, a mode selection module, a timing module, an MP3 module and batteries respectively electrically connected to the microprocessor, as well as a speaker electrically connected to the MP3 module; wherein, the mode of the present invention can at least be selectively set as eye heating massage mode, eye humidity control mode, airbag massage mode, vibrating massage mode, etc., and the above modes can be used alone or in combination. In addition, the control modes of the present invention may be defined as physical button mode or touch screen control mode according to the conventional modes.

Figure 5:
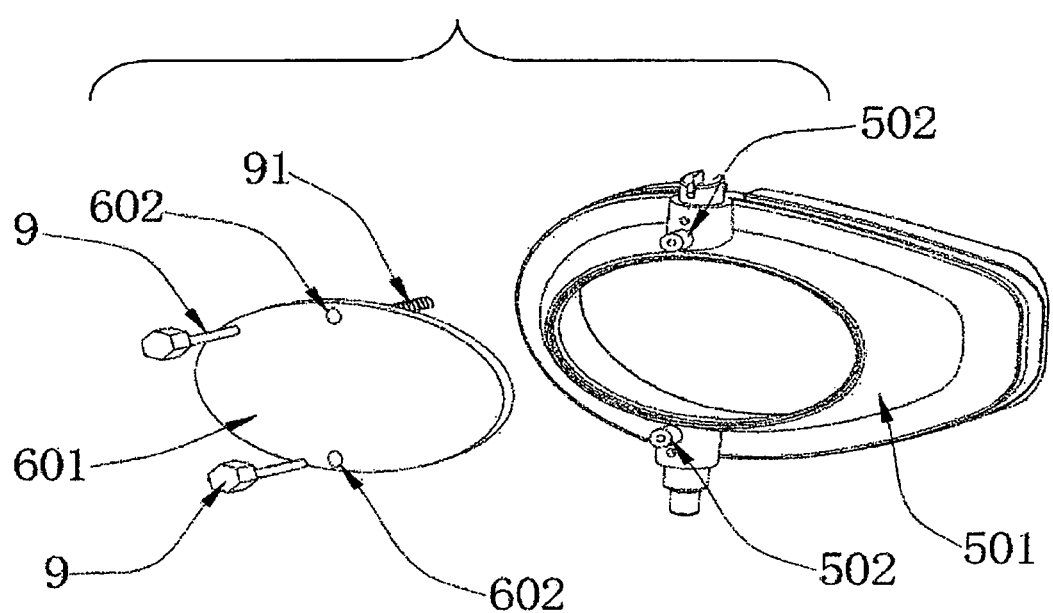
FIG. 5 is a structural view of another embodiment of the humidity-control device shown in FIG. 1.

As shown in FIG. 5, as a variation of the present invention, it could be visible heating integrated health care glasses, comprising shells, control boxes and head fixing parts. The shells are connected to the head fixing parts, being fixed in front of the head through the fixing parts; the shells are provided with lens holes in which eye cups are equipped; the shells are equipped with lens holes which are located in the place where the shells correspond to the eyes. The lens holes are provided with eye cups inside, with the front of the eye cups connected to the lens and the back of eye cups connected to the heating blinders. The shells are equipped with vibrating motors inside, and the heating blinders and the vibrating motors are connected with the control boxes through cables.

Preferably, the visible heating integrated health care glasses feature a partial head-mounted design. The shells are fixed to the head through the head fixing parts, while the control boxes are not fixed to the head but are set outside the head-mounted part, so that the users can operate the control boxes by hand freely.

Preferably, the visible heating integrated health care glasses feature a total head-mounted design. The control boxes are connected to the head fixing parts, being fixed at the back of the head through the head fixing parts, and equipped opposite to the shells.

Preferably, the heating blinders comprise tubular blinder bodies. The tubular blinder bodies enclose the first channel. The tubular blinder bodies comprise heating parts. The heating parts comprise ring grooves and heating rings equipped therein. The blinder bodies also comprise massage parts connected to the heating parts, and the massage parts comprise massage layers. Massage balloons are preferably provided on the massage layers so as to achieve better effects of massage. Preferably, the eye cups comprise tubular cup bodies which enclose the second channel and are hinged to the lens holes so as to make the cup bodies movable relatively to the shells and adjustable according to face shapes of users. The cup bodies are equipped with the lens in the front end, with its rear end snap-fitted with the heating blinders.

When using the visible heating integrated health care glasses of the present invention, the heating blinders correspond to the human eyes, with the massage layers of the massage parts closely sticking to the skin around the eye. The vibrating motors trigger the vibration of the visible heating integrated health care glasses, thus vibrating the massage part so as to take a massage effect onto the eye skins to alleviate fatigue. When the heating rings are heated up, the infrared rays are generated to give a hot pack onto the eyelids and under-eye skins to prevent dark circles and under-eye bags. The heat emitted from the heating rings heats up the skin around the eye, making it sweat. The sweat turns into water vapor, filling in the first channel and the second channel so that the heat blinders, the eye cups and the lens form a wet room for eyes which can treat dry eye syndrome.

The wet rooms of the existing glasses are closed, so the glasses will fog up when the water vapor contacts relatively cold wet room walls and make it impossible for users to see as normal. To solve this problem, the inventor has tried for many times, finding that when there is some space between the lens and the eye cups, it can achieve the effects of preventing fogging, normal eye viewing and treatment of dry eye syndrome. The water vapor moves forward through the first channel into the second channel. Due to the heat generated by the heating rings, the temperatures of the heating blinders and the eye cups are relatively high, so it will not turn water vapor into fog. Located at the forefront, the lens exchange heat with the outside environment, and it has a relatively low temperature, and the water vapor may turn into fog when it contacts the lens, so by providing an anti-fog channel, namely, a space, between the lens and the eye cups, the water vapor will not contact the lens but will be emitted to the outside of the wet room. The space 8 also narrows the temperature difference between inside and outside of the wet room nearby, which also can avoid fogging. The space should not be too large or too small, if it is too large, it may make drain the water vapor too fast, so that it will not make the wet room take effect; if it is too small, it may still generate fog so that it cannot avoid fogging and offer normal eye viewing. Therefore, the space between the lens and the eye cups should preferably be 0.5-3 mm, more preferably 1-2 mm. The space of such width not only can be taken as an anti-fog channel to prevent fogging in the eye cups, but also can maintain a large amount of moisture in the first channel and the second channel so as to treat the dry eye syndrome.

Preferably, as shown in FIG. 5, in order to better adjust the width of the space, so as to achieve the purpose of adjusting the humidity, the visible heating integrated health care glasses are also equipped with a humidity-control device. The humidity-control devices comprise fixing holes 602 equipped on two sides of the lens 601, lugs 502 equipped corresponding to the fixing holes 602 and on the two sides of the eye cups 501 respectively, knob screws 9 and springs 91. The springs 91 are disposed between the fixing holes 602 and the lugs 502, the lugs 502 also have mounting holes, and the knob screws 9 pass through the fixing holes 602 and the springs 91 so as to be screwed with the mounting holes.

Furthermore, in order to better adjust the width between the lens and the eye cups, and to attain an ideal humidity, the nuts of the knob screws may have a regular-polygon structure, and preferably a regular-hexagon structure.

EMBODIMENTS

First, users can adjust the length of bandages according to the size of the head and wear the glasses. After that, the users can see things through windows which will not affect the normal work or life. In addition, the users also can do eye exercises by replacing the lens in the windows.

Second, the users can choose various massage modes according to actual needs to achieve different effects, or realize customized massage modes by combining different massage modes, such as:

Eye heating massage mode: carbon fiber heating filaments equipped at the peripheries of the windows are heated, and meanwhile, the temperature is detected through temperature sensors. When the temperature reaches a certain value (the temperature according to the invention is 42 degrees), heating will be stopped, and when reduction of the temperature is detected, the carbon fiber heating filaments will be activated again to continue to be heated, thus expanding eye blood capillaries and increasing blood circulations via a constant temperature control to achieve the purpose of eliminating eye fatigue.

Eye humidity-control mode: firstly, it activates the carbon fiber heating filaments to make it heat up, and then the heat will gather in the adjusting chamber. As the water sponges on both sides of the adjusting chamber contain a certain amount of water, the water will be evaporated to produce moisture as the temperature in the adjusting chamber rises. Furthermore, humidity sensors keep detecting the humidity in the adjusting chamber, and when the humidity reaches the preset value, it will stop heating up of carbon fiber heating filaments; secondly, the moisture can be discharged through humidity control grooves in the adjusting chamber. Users can adjust the humidity by sliding the humidity-control upper leaf or the humidity-control lower leaf to shield or partly shield the humidity control grooves, so as to gather most of moisture into the adjusting chamber or slowly discharge the moisture.

Furthermore, to help add liquids that can turn into moisture to water sponges, the left and right blinders are both equipped with through-holes, and the through-holes are connected to three-way pipes arranged on one side of the adjusting chamber, so the water storage sponges are connected to the three-way pipes. Therefore, the users can add liquids to the water storage sponges through the through-holes. Besides, to make the glasses more convenient, the present invention also provides a dropper that matches the through-holes to help add liquids.

Airbag massage mode: after this mode is enabled, solenoid valves connected to the airbags will be activated. At the same time, air pumps start to inflate the airbags via the solenoid valves. It will release the air after each inflation is completed, and await the next inflation. It repeats the process, until the timing under the mode is completed.

Vibrating massage mode: after this mode is enabled, vibrating motors start vibrating massage. It needs to be noted that the vibrating motors can realize different frequencies of vibration, so as to achieve various massage effects.

In addition, for the convenience of wearing, the left and right blinders according to the present invention feature a rotating structure. Specifically, the left blinder and the right blinder are equipped with bolt holes at the opposite sides so that the bolt passes through the bolt holes to connect the left blinder and the right blinder, enabling the left blinder and the right blinder to rotate along the bolt so as to realize foldability of the eye-care glasses.

For those practitioners skilled in this field, a variety of corresponding modifications and variations can be made on the basis of the technical solutions and the concept of the present invention mentioned above. However, all the modifications and variations should be covered in the protection scope of the Claims of the present invention.

What is claimed is:

1. A pair of eye-care glasses, comprising blinders equipped with windows and control circuits, characterized in that the eye-care glasses also comprise heating devices and humidity-control devices equipped at the peripheries of the windows, wherein the control circuits are electrically connected to the heating devices and the humidity-control devices; the blinders comprise a left blinder, a right blinder and a rotating device, wherein each of a side of the left blinder facing towards the right blinder and a side of the right blinder facing towards the left blinder is equipped with at least one bolt hole: the rotating device consists of a bolt and a rotating cap, and the bolt is connected into the at least one bolt hole of the left blinder and the at least one bolt hole of the right blinder, to make the left blinder and the right blinder rotate along the bolt.

2. The eye-care glasses of claim 1, wherein the heating devices comprise carbon fiber heating filaments and temperature sensors, the peripheries of the windows are provided with grooves used to install the carbon fiber heating filaments, and the carbon fiber heating filaments and the temperature sensors are electrically connected to the control circuits.

3. The eye-care glasses of claim 1, wherein the humidity-control devices comprise an adjusting chamber, a humidity-control upper leaf, a humidity-control lower leaf, a water storage sponge and humidity sensors, wherein the humidity-control upper leaf and the humidity-control lower leaf are flexibly connected to the top and bottom of the adjusting chamber respectively, the water storage sponge is distributed on side walls inside the adjusting chamber, and the humidity sensors and the control circuits are electrically connected.

4. The eye-care glasses of claim 3, wherein each of the top and bottom of the adjusting chamber is equipped with a humidity-control groove used to expel the moisture in the adjusting chamber.

5. The eye-care glasses of claim 4, wherein the top and bottom of the adjusting chamber are respectively equipped with an upper guide groove and a lower guide groove, and the humidity-control upper leaf and the humidity-control lower leaf are flexibly connected into the upper guide groove and the lower guide groove respectively; the water storage sponge is equipped in a semi-closed space formed by the upper guide groove and the lower guide groove.

6. The eye-care glasses of claim 5, wherein each of the upper guide groove and the lower guide groove is equipped with a positioning bar, and the humidity-control upper leaf or the humidity-control lower leaf is equipped with positioning grooves matched with the positioning bars.

7. The eye-care glasses of claim 3, wherein one side of the adjusting chamber is equipped with three-way pipes which are connected to the water storage sponge.

8. The eye-care glasses of claim 1, wherein a massage airbag device is equipped inside the blinders, and the massage airbag device comprises airbags, an air pump and a solenoid valve, wherein the airbags are connected to one end of the solenoid valve, one end of the air pump is connected to another end of the solenoid valve, and the control circuits are electrically connected to the air pump and the solenoid valve.

9. The eye-care glasses of claim 1 or 8, wherein vibrating motors are also equipped inside the blinder: the vibrating motors are electrically connected to the control circuits.

10. The eye-care glasses of claim 1, wherein the humidity-control devices comprise fixing holes equipped on two sides of each lens of the glasses in front of a corresponding eye cup, lugs equipped on two sides of each eye cup corresponding to the fixing holes, knob screws and springs; the springs are disposed between the fixing holes and the lugs, the lugs also have mounting holes, and the knob screws pass through the fixing holes and the springs so as to be screwed with the mounting holes.

11. The eye-care glasses of claim 10, wherein nuts of the knob screws feature a regular-polygon structure.

\* \* \* \* \*